US008184648B2

(12) United States Patent
Allan et al.

(10) Patent No.: US 8,184,648 B2
(45) Date of Patent: May 22, 2012

(54) METHOD AND APPARATUS FOR IMPLEMENTING CONTROL OF MULTIPLE PHYSICALLY DUAL HOMED DEVICES

(75) Inventors: David Allan, Ottawa (CA); Peter Ashwood Smith, Hull (CA)

(73) Assignee: Rockstar Bidco, LP, New York, NY (US)

( * ) Notice: Subject to any disclaimer, the term of this patent is extended or adjusted under 35 U.S.C. 154(b) by 251 days.

(21) Appl. No.: 12/487,407

(22) Filed: Jun. 18, 2009

(65) Prior Publication Data
US 2010/0322263 A1 Dec. 23, 2010

(51) Int. Cl.
*H04L 12/28* (2006.01)
(52) U.S. Cl. ........ 370/403; 370/219; 370/256; 370/351; 370/401; 709/238
(58) Field of Classification Search .................. 370/219, 370/256, 351, 401, 403; 709/238
See application file for complete search history.

(56) References Cited

U.S. PATENT DOCUMENTS

| | | | | |
|---|---|---|---|---|
| 5,299,312 A * | 3/1994 | Rocco, Jr. | .............. | 714/4.12 |
| 5,953,314 A * | 9/1999 | Ganmukhi et al. | ............ | 370/220 |
| 6,246,692 B1 * | 6/2001 | Dai et al. | ...................... | 370/438 |
| 7,246,168 B1 * | 7/2007 | Bales | ............................ | 709/228 |
| 7,411,963 B2 * | 8/2008 | Ward et al. | ..................... | 370/398 |
| 7,639,605 B2 * | 12/2009 | Narayanan et al. | ........... | 370/219 |
| 7,643,468 B1 * | 1/2010 | Arregoces et al. | ............ | 370/351 |
| 7,751,416 B2 * | 7/2010 | Smith et al. | ..................... | 370/410 |
| 7,925,817 B2 * | 4/2011 | Uehara et al. | ................. | 710/316 |
| 2002/0019958 A1 * | 2/2002 | Cantwell et al. | ................ | 714/11 |
| 2002/0023170 A1 * | 2/2002 | Seaman et al. | ................ | 709/235 |
| 2002/0191250 A1 * | 12/2002 | Graves et al. | ................. | 359/128 |
| 2003/0185149 A1 | 10/2003 | Daniell et al. | | |
| 2004/0100970 A1 * | 5/2004 | Gerdisch et al. | ......... | 370/395.53 |
| 2005/0066216 A1 * | 3/2005 | Hebbar et al. | ..................... | 714/1 |
| 2005/0276215 A1 * | 12/2005 | Kitani et al. | .................. | 370/217 |
| 2007/0047436 A1 * | 3/2007 | Arai et al. | ...................... | 370/219 |
| 2007/0076719 A1 | 4/2007 | Allan et al. | | |
| 2008/0225695 A1 * | 9/2008 | Balus et al. | ................... | 370/216 |
| 2008/0239946 A1 * | 10/2008 | Morita | .......................... | 370/217 |
| 2008/0279096 A1 * | 11/2008 | Sullivan et al. | .................. | 370/221 |
| 2008/0304477 A1 * | 12/2008 | Froroth et al. | ................ | 370/360 |
| 2009/0168647 A1 | 7/2009 | Holness et al. | | |
| 2009/0168671 A1 | 7/2009 | Holness et al. | | |
| 2010/0020680 A1 * | 1/2010 | Salam et al. | .................... | 370/225 |
| 2010/0142544 A1 * | 6/2010 | Chapel et al. | ................. | 370/401 |
| 2010/0189117 A1 * | 7/2010 | Gowda et al. | ................. | 370/401 |
| 2010/0284413 A1 * | 11/2010 | Abdullah et al. | ............. | 370/401 |

* cited by examiner

OTHER PUBLICATIONS

International Search Report and Written Opinion from corresponding PCT application PCT/CA2010/000935.

*Primary Examiner* — Ayaz Sheikh
*Assistant Examiner* — Andrew C Lee
(74) *Attorney, Agent, or Firm* — Withrow & Terranova, PLLC

(57) ABSTRACT

A ring control protocol is used to establish a separate control plane for a plurality of physically dual homed devices to enable collections of dual homed devices to be represented by a single pair of addresses into the attached routed Ethernet network. The gateway devices analyze the passing ring control packets to create direct mappings for data packets to the routed Ethernet network. Thus, although the dual homed devices are treated as a ring from a control perspective, the data path is implemented to be direct so that data packets continue to flow directly from the dual homed devices to each of the attached gateway devices. In one embodiment, each of the gateway devices implements a virtual switch and advertises the MAC address of the virtual switch into the routed Ethernet network rather than the MAC addresses of each of the attached Ethernet Switch Units.

16 Claims, 4 Drawing Sheets

METHOD AND APPARATUS FOR IMPLEMENTING CONTROL OF MULTIPLE PHYSICALLY DUAL HOMED DEVICES

TECHNICAL FIELD

The present invention relates to communication networks and, more particularly, to a method and apparatus for implementing control of multiple physically dual homed devices.

BACKGROUND

Data communication networks may include various switches, routers, hubs, and other devices coupled to and configured to receive data and forward the data on the network. These devices will be referred to herein as "network elements." A network element is generally not a consumer of the data, but rather is used to receive and forward data so that the data may pass through the network. Data is communicated through a network by enabling the network elements to pass protocol data units, such as frames, packets, cells or segments, between each other over communication links. A particular protocol data unit may be handled by multiple network elements and cross multiple communication links as it travels between its source and its destination over the network.

The various network elements on the communication network communicate with each other using predefined sets of rules, referred to herein as protocols. Different protocols are used to govern different aspects of the communication, such as how signals should be formed for transmission between the network elements, various aspects of what the protocol data units should look like, how protocol data units should be handled or routed through the network by the network elements, and how information such as routing information should be exchanged between the network elements.

A network service provider will generally implement one or more data centers to enable customers to connect to a communication network such as the Internet. Likewise, in an enterprise, a data center may be used to house servers that enable users to connect to the corporate network or which provide other services on the network. Example services include database services, email services, etc.

In a data center, a large number of servers (e.g. 24 servers) may be housed in a rack and connected to an Ethernet Switch Unit which connects the servers to a communication network. Typically, the Ethernet Switch Unit will be co-located with the rack of servers. The Ethernet switch unit will then connect to a large Gateway switch which will connect the Ethernet switch unit to higher bandwidth network such as a routed Ethernet network.

FIG. 1 shows an example data center in which servers 10 connect to one or more Ethernet switch units 12, which in turn are connected to gateways 14. The gateways 14 provide connectivity to a routed Ethernet network 16. The Ethernet switch units will generally be dual-homed to a pair of gateway switches so that, if one of the gateway switches should fail, the other gateway can assume responsibility for forwarding traffic into the routed Ethernet network. For example, in FIG. 1, each of the Ethernet switch units 12 are connected to two different gateways (e.g. dual homed) to a pair of gateway switches 14. The gateway switches may individually assume responsibility to represent particular ESUs into the routed Ethernet network or, alternatively, may collaboratively represent the ESUs into the routed Ethernet network by treating the links from the ESUs to the gateways as a split multi-link trunk.

Although it is possible to envision multiple ESUs in a chain connected to a pair of gateway nodes, such a configuration is vulnerable to multiple failures. Hence dual homing of individual switches directly to the gateways is desirable since the configuration is less susceptible to failure.

Large data centers may require layer two connectivity for communities of 10s to 100s of thousands of servers. To enable this configuration to be able to scale, one of the key metrics to consider is the number of MAC addresses the gateway is required to advertise into the routed Ethernet network to represent the set of subtending servers. Specifically, when the ESU is connected directly to the gateway, the gateway will need to advertise the MAC address of the port via which the ESU is reached into the routed Ethernet network Normally as the number of Ethernet switch units increases, the associated number of ports, and hence the number of MAC addresses being advertised into the routed Ethernet network (e.g. an Ethernet network implemented using 802.1aq Shortest Path Backbone Bridging, although this may also apply to 802.1ah spanning tree controlled Ethernet networks) may become excessive and expensive for the core to maintain. Accordingly, it would be advantageous to provide a way to reduce the number of MAC addresses that is required to be advertised into the routed Ethernet network.

SUMMARY OF THE INVENTION

One or more ring control protocol instances are run on the multiple physically dual homed devices in such a way that enables collections of dual homed devices to be represented by a single pair of addresses into the attached routed Ethernet network. The gateway devices analyze the passing ring control packets to create direct mappings for data packets to the routed Ethernet network. Thus, although the dual homed devices are treated as a ring from a control perspective, the data path is implemented to be direct so that data packets continue to flow directly from the dual homed devices to each of the attached gateway devices. Each of the gateway devices implements one or more virtual switches, which each serve to aggregate traffic from multiple attached ESUs into the routed Ethernet network. Each virtual switch advertises its own MAC address into the routed Ethernet network rather than the MAC addresses of each of the attached Ethernet Switch Units so that fewer MAC addresses will be advertised by each of the gateways. When resiliency is provided for by a peer gateway, frames may be send to and received from the ESU directly or via the peer gateway (in failure scenarios). Frames that are received from the Ethernet switch units are encapsulated at the virtual switch using a new Ethernet header identifying the virtual switch as the source of the data packets. In the reverse direction, frames of data will be addressed to the virtual switch, which will demux packets using the C-MAC Ethernet header to pass the frames onto the correct output port to the correct Ethernet switch unit. By running a separate control plane between the Ethernet switch units and the gateway, a set of Ethernet switch units is able to be represented into the routed Ethernet network using a pair of MAC addresses, while enabling data paths to continue to flow directly between the Ethernet switch units and the routed Ethernet network.

BRIEF DESCRIPTION OF THE DRAWINGS

Aspects of the present invention are pointed out with particularity in the appended claims. The present invention is illustrated by way of example in the following drawings in which like references indicate similar elements. The following drawings disclose various embodiments of the present invention for purposes of illustration only and are not intended to limit the scope of the invention. For purposes of clarity, not every component may be labeled in every figure. In the figures:

DETAILED DESCRIPTION

Figure 1:
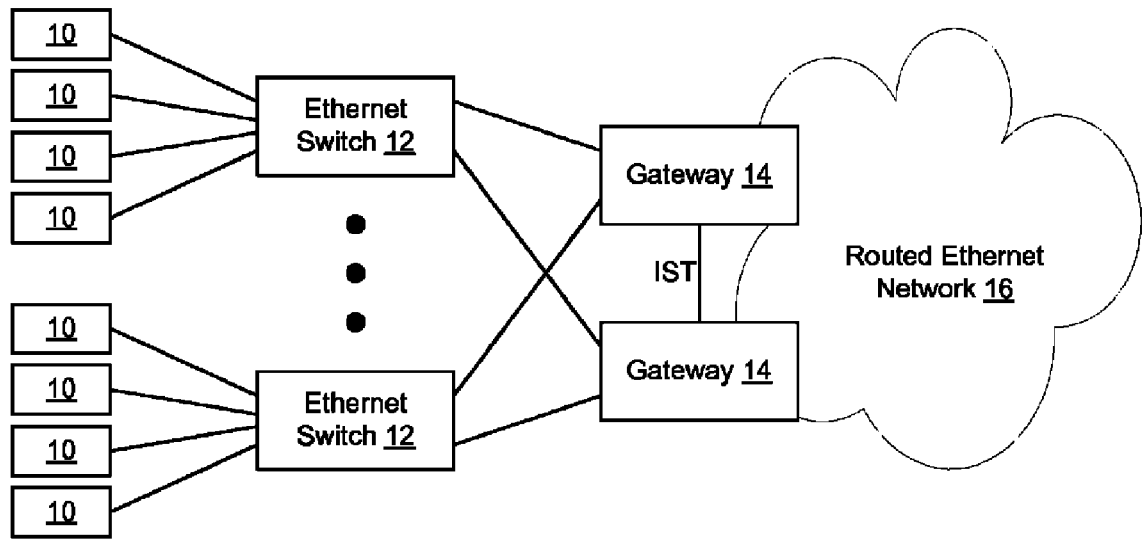
FIG. 1 is a functional diagram of a reference network showing a dual homed connection between Ethernet Switch Units and a pair of gateways.
Figure 2:
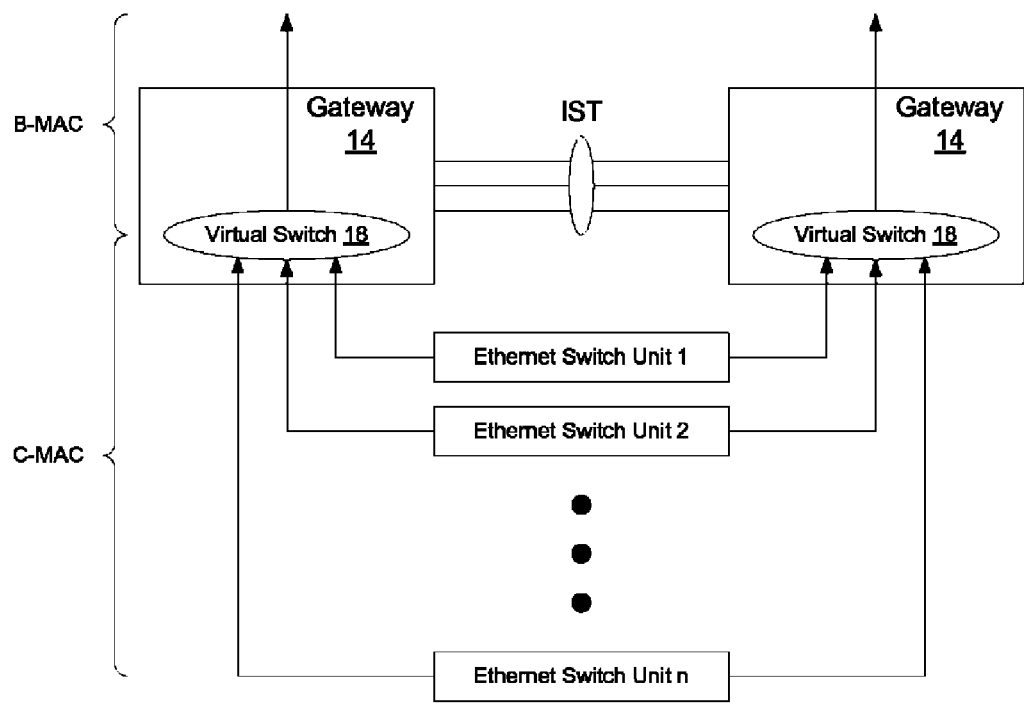
FIG. 2 is a functional block diagram showing physical dual homed Ethernet switch units interconnecting with a pair of gateway switches.

FIG. 2 is a functional block diagram showing physical dual homed Ethernet switch units interconnecting with a pair of gateway switches. As shown in FIG. 2, each of the Ethernet switch units connects via one or more links to two or more Gateways 14. According to an embodiment, each of the gateways implements at least one virtual switch 18 that summarizes traffic from a plurality of Ethernet switch units into the routed Ethernet network 16. In one embodiment, the virtual switch performs Mac-in-Mac encapsulation to add a B-MAC Ethernet header to the traffic as described in IEEE 802.1ah. Each gateway may implement multiple virtual switches, each of which is responsible for handling traffic for a set of the attached Ethernet switch units. By implementing a virtual switch, sets of subtending ESUs that have a common peer gateway may be represented by a single MAC address into the routed Ethernet network rather than requiring each ESU to be individually represented into the routed Ethernet network. Hence, the number of MAC addresses advertised into the core network may be reduced to increase scalability of the network.

According to an embodiment of the invention, one or more instances of a separate control plane is implemented between the virtual switches and attached set of physically dual homed devices (e.g. Ethernet switch units). The control plane, in one embodiment, is implemented using a ring control protocol so that control messages, e.g. link state advertisements, will follow the logical ring rather than following the data path on the network. By utilizing a ring control protocol, control messages may be exchanged between the set of attached physical devices while enabling the set of attached physical devices to be represented into the attached routed Ethernet network using a pair of MAC addresses. However, whereas the control plane is implemented using a ring architecture, the data path from each physically dual homed device to the associated gateways remains point-to-point so that the selection of a ring-based control protocol does not affect the data traffic patterns on the network.

It should be noted that simply having a common MAC address for all devices connected to the gateway node in many cases is not sufficient, this is because under failure of the node the recovery actions may not be aligned. There may be customers directly attached to the switch, or sets of switches for which there is a different peer gateway in the dual homed arrangement. Hence a MAC address is assigned for a set of subtending switches that have a common recovery behavior under failure.

Ethernet Shared Protection Rings (E-SPRING) is a protocol designed to be used to control an Ethernet ring network having a group of serially interconnected nodes. E-SPRING is defined as ITU-T SG15/Q9, G.8032, which specifies how the nodes on the ring should handle unicast, multicast, and broadcast frames. It also specifies multiple service classes, failure handling, and other aspects of how traffic should be forwarded by nodes on the Ethernet ring. The manner in which an Ethernet ring operates is also described in greater detail in U.S. patent application Ser. No. 12/027,942, entitled Method And Apparatus For Controlling A Set Of Ethernet Nodes Interconnected To Form One Or More Closed Loops, filed Feb. 7, 2008, the content of which is hereby incorporated herein by reference. In one embodiment, the control plane associated with the interconnection between the gateways and Ethernet switch units is implemented using a ring control protocol. U.S. patent application Ser. No. 12/344,355, filed Dec. 26, 2008, describes a way of enabling a network implemented using a ring control protocol to be dual homed into an Ethernet network implementing a spanning tree control protocol, and U.S. patent application Ser. No. 12/344,362, filed Dec. 26, 2008, describes a way of enabling a ring network implemented using a ring control protocol to be dual homed into an Ethernet network implementing traffic engineered trunks. The content of each of these applications is hereby incorporated herein by reference.

Figure 3:
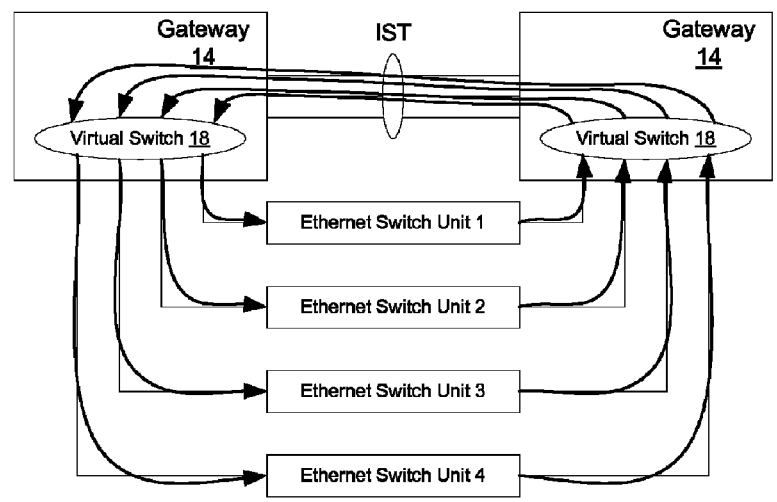
FIG. 3 shows the flow of control information between the network devices arranged as shown in FIG. 2 according to one embodiment of the invention.
Figure 4:
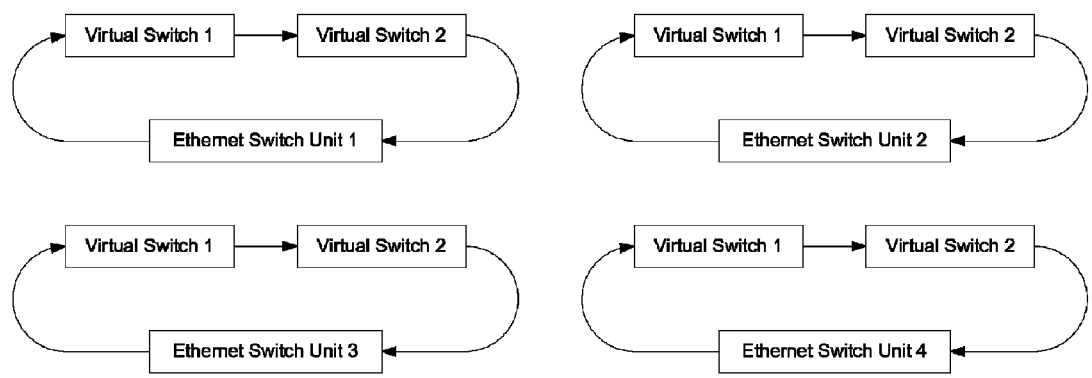
FIG. 4 shows the logical flow of control information in the embodiment of FIG. 3.

FIG. 3 shows one example of how a ring control protocol may be used according to one embodiment of the invention. In this embodiment, each gateway has implemented a virtual switch that summarizes routes from the multiple Ethernet switch units into a single BMAC for advertisement on the network. In this example, a separate ring protocol instance is used for each Ethernet Switch Unit. For example, as shown in FIG. 4, a separate ring control instance may be used to create a logical control ring including one of the virtual switch instances in each of the gateways, as well as one of the Ethernet switch units. Thus, in FIG. 4, a first ring control protocol instance is used to control Ethernet switch 1 and includes Ethernet Switch Unit 1, virtual switch 1, and virtual switch 2. Likewise, a second ring control protocol instance is used to control Ethernet switch 2. In this embodiment, the second ring control protocol instance includes Ethernet switch 2, virtual switch 1, and virtual switch 2.

The ring control protocol enables traffic to be forwarded from the Ethernet switch unit to the correct gateway in a persistent manner so that link failures between the Ethernet switch units and the gateways is transparent to the routed network. For example, assume that traffic from Ethernet switch unit 1 was to be forwarded by the left gateway in FIG. 2 onto the routed Ethernet network. The ring control protocol may implement a blocking port on the port leading to the right gateway, so that traffic flows from the Ethernet switch unit to the left gateway. If there is a failure on the link between Ethernet Switch Unit 1 and the left gateway, the ring control protocol will automatically remove the blocking port and move the blocking port to be adjacent the failure. This will cause the Ethernet switch unit to forward traffic out toward the gateway on the right. The virtual switch in the right gateway will know that it is not responsible for forwarding traffic into the routed Ethernet network and will forward the traffic along the ring over the IST to the left gateway. The virtual switch in the left gateway will thus receive the traffic from the Ethernet switch unit 1 via the IST and forward the traffic into the routed Ethernet network. By implementing a ring control protocol, local failures between the Ethernet switch units and the gateway may be hidden from the routed Ethernet network, so that each end of the ring appears as an invariant B-MAC.

Figure 8:
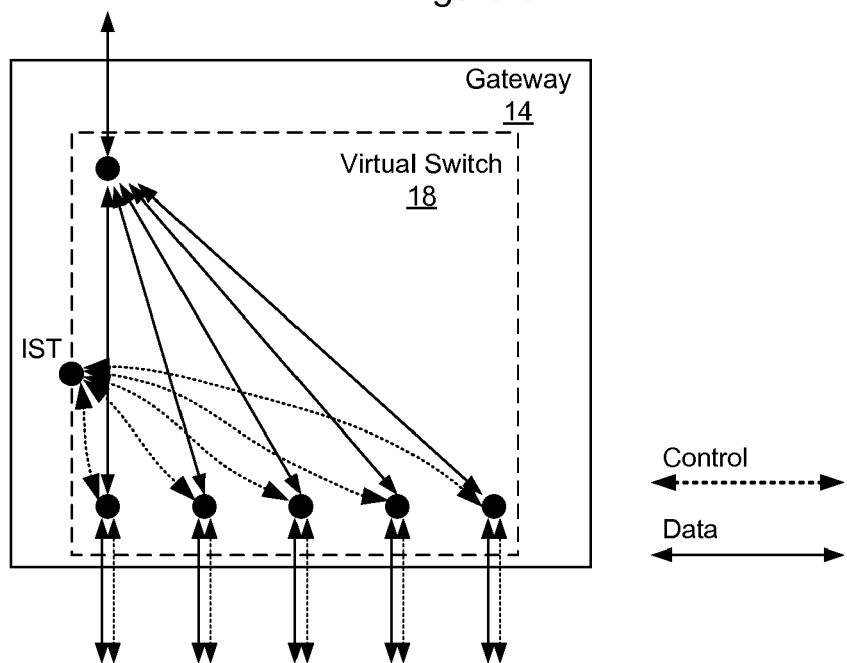
FIG. 8 shows the flow of data and the flow of control information through one of the gateways according to the embodiment of the invention shown in FIGS. 3-4.

Although the control traffic flows as shown in FIG. 3, the data traffic from each of the switch units is passed to the selected virtual switch and is passed from the virtual switch onto the attached routed Ethernet network. FIG. 8 shows an example of how the control traffic and data traffic would be handled by a virtual switch. As shown in FIG. 8, the virtual switch will forward data traffic onto the routed Ethernet network and will forward control traffic over the IST to enable the control traffic to pass over the ring to the other virtual switch. Of course, as described above, under failure conditions there may be instances where the virtual switch will also forward data traffic over the IST. Accordingly, each virtual switch will only forward traffic for that set of ESUs that it is responsible to represent into the routed Ethernet network.

Figure 5:
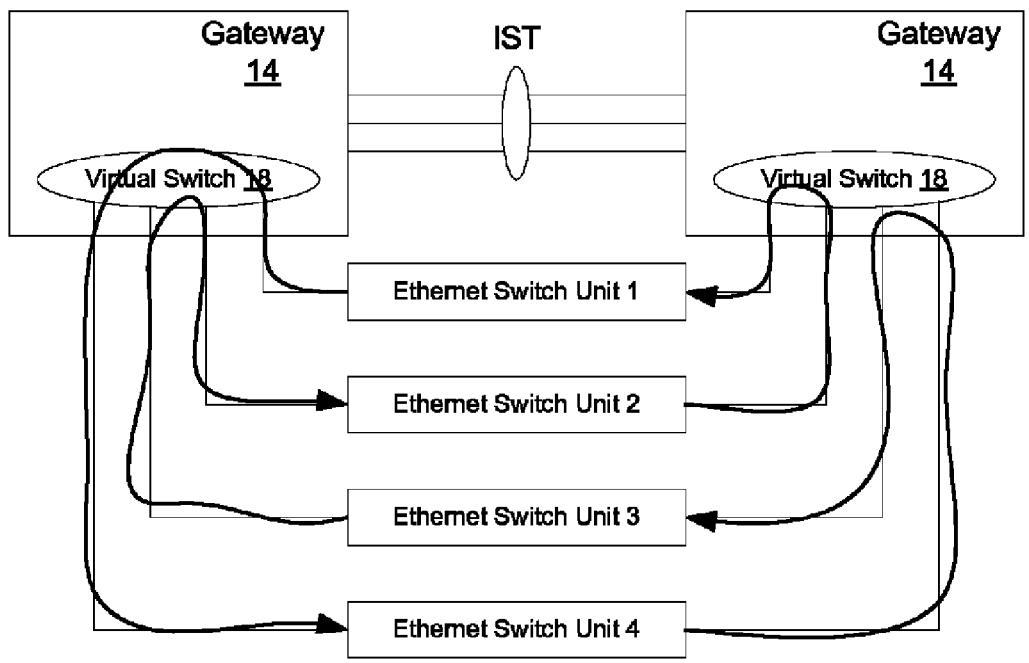
FIGS. 5-6 show the flow of control information between the network devices arranged as shown in FIG. 2 according to another embodiment of the invention.
Figure 6:
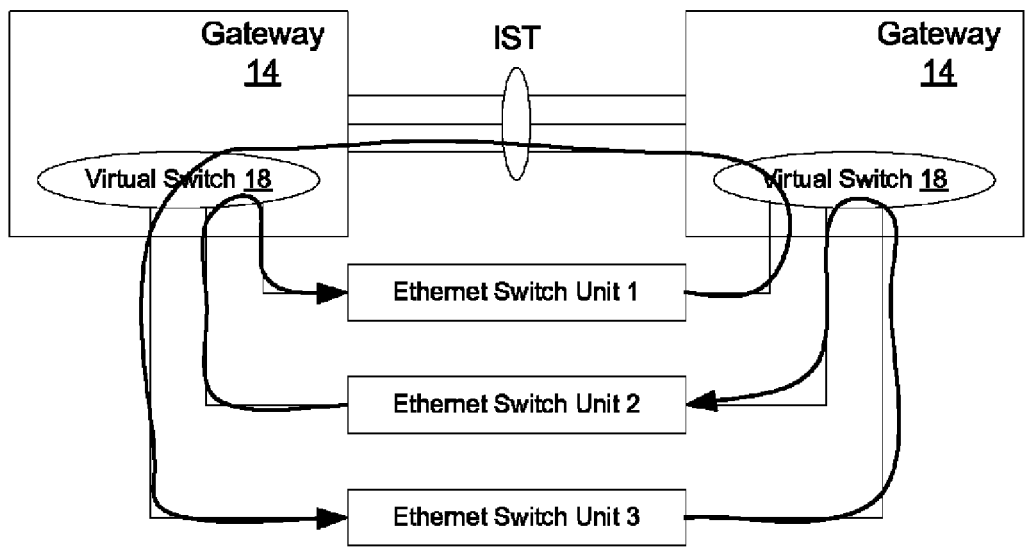
Figure 7:
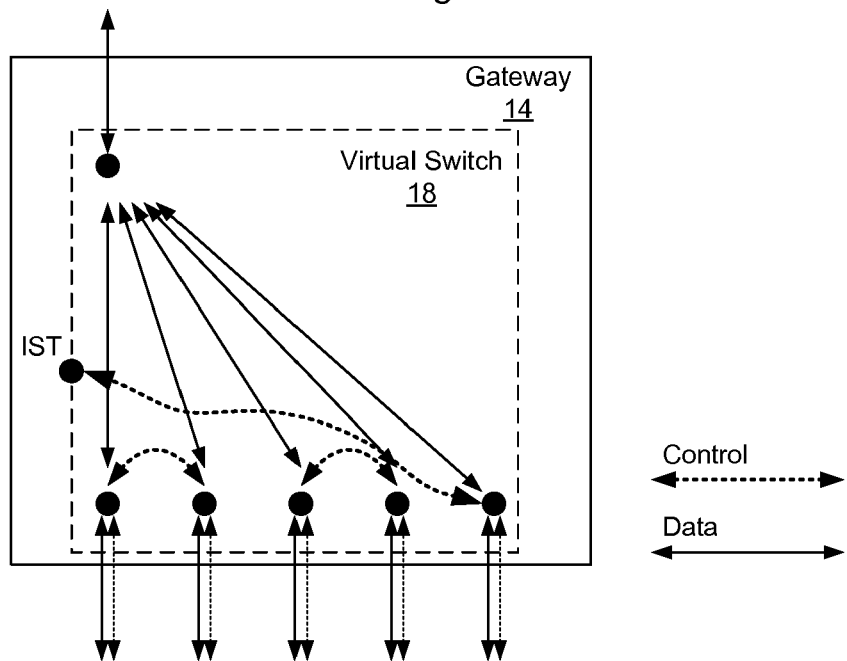
FIG. 7 shows the flow of data and the flow of control information through one of the gateways according to the embodiment of the invention shown in FIGS. 5-6.

FIGS. 5-7 show another embodiment where groups of Ethernet switch units are logically formed into a single ring for control purposes by causing the gateway switches to u-turn control packets to enable multiple Ethernet switch units to exist on a common control ring. In the embodiment shown in FIG. 5, there are an even number of Ethernet switch units, which enables each of the gateway switches to directly interconnect each of the Ethernet switch units on the ring. FIG. 6 shows another example in which there is an odd number of Ethernet switch units. In this instance one of the branches of the logical ring will need to extend over the Inter-switch trunk to complete the ring. Although the example shown in FIG. 6 has the control traffic being passed over the IST, the invention is not limited in this regard as the control traffic could instead be passed by the virtual switch over the attached routed network.

FIG. 7 shows the difference between the data path and the control path in a gateway node. As shown in FIG. 7, interconnecting the Ethernet switch units in a logical ring for control purposes only affects the flow of control packets between the Ethernet switch units. Specifically, in the embodiment shown in FIG. 7 the control packets are looped back to enable a group of Ethernet switch units to be logically interconnected in a ring (e.g. as shown in FIG. 5 or 6) so that a ring control protocol may be used to manage these devices. However, the data path associated with the Ethernet switch units is still point to point so that, when the gateway receives a data packet, it will forward the data packets directly onto the PLSB network in a normal manner. Thus, implementing the control plane using a ring control protocol does not affect the manner in which the gateway switches handle data traffic on the network or how the gateway switches forward data onto the PLSB network.

The virtual switch 18 performs MAC learning to learn MAC addresses reachable via the attached ESU by watching the unique port the ESU is attached to. When the gateway receives a data packet from an attached Ethernet switch unit, it will pass the packet to the virtual switch, which will perform BMAC encapsulation to enable the packet to be forwarded over the attached routed Ethernet network. In the reverse direction, when the gateway receives a packet from the routed Ethernet network, the virtual switch will read the client MAC address and use the mapping to select an output port to forward the packet to the correct Ethernet switch unit.

As discussed above, each of the Ethernet Switch Units aggregates traffic from multiple clients. Traffic from that ESU may then be forwarded to a particular gateway or, alternatively, may be forwarded to virtual switches on two or more gateways. Likewise, traffic from a particular ESU may be forwarded to two or more virtual switches implemented on the same gateway. Traffic from a particular ESU may be transmitted in one or more VLANs to enable traffic to be directed to different virtual switches within the same ESU, so that each ESU can aggregate a portion of the traffic for the ESU into the attached routed Ethernet network.

The functions described above may be implemented as a set of program instructions that are stored in a computer readable memory and executed on one or more processors on the computer platform. However, it will be apparent to a skilled artisan that all logic described herein can be embodied using discrete components, integrated circuitry such as an Application Specific Integrated Circuit (ASIC), programmable logic used in conjunction with a programmable logic device such as a Field Programmable Gate Array (FPGA) or microprocessor, a state machine, or any other device including any combination thereof. Programmable logic can be fixed temporarily or permanently in a tangible medium such as a read-only memory chip, a computer memory, a disk, or other storage medium. All such embodiments are intended to fall within the scope of the present invention.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense.

What is claimed is:

1. A method of implementing control of multiple network devices, the multiple network devices being physically dual homed on a pair of gateways configured to provide interconnectivity between the multiple network devices and a routed Ethernet network, the method comprising the steps of:

implementing, by each gateway, at least one virtual switch instance to represent the multiple dual homed network devices into the routed Ethernet network; and implementing at least one ring-based control protocol instance between the at least one virtual switch instance of each gateway and the multiple physically dual homed network devices to enable the virtual switches to coordinate representation of the dual homed network devices into the routed Ethernet network, wherein each gateway U-turns control traffic received from the dual homed network devices to implement a logical ring including the virtual switch instance of each gateway and the multiple physically dual homed network devices.

2. The method of claim 1, wherein a first ring-based control protocol instance is implemented between a first virtual switch instance on a first of the gateways, a second virtual switch instance on a second of the gateways, and a first of the multiple physically dual homed network devices to enable the first gateway and second gateway to coordinate representation of the first dual homed network device into the routed Ethernet network.

3. The method of claim 2, wherein a second ring-based control protocol instance separate from the first ring-based control protocol instance is implemented between the first virtual switch instance on the first gateway, the second virtual switch instance on the second gateway, and a second of the multiple physically dual homed network devices to enable the first gateway and second gateway to coordinate representation of the second dual homed network device into the routed Ethernet network.

4. The method of claim 1, wherein a separate ring-based control protocol instance is implemented for each of the dual homed network devices.

5. The method of claim 1, wherein the gateways are connected by an inter-gateway trunk, and wherein if the unified ring-based control protocol instance is implemented to coordinate representation of an odd number of dual homed network devices, the inter-gateway trunk will be used to close the logical ring.

6. The method of claim 1, wherein control traffic and data traffic are treated differently by the gateways.

7. The method of claim 1, wherein the virtual switch instance summarizes traffic into the routed Ethernet network.

8. The method of claim 7, wherein each virtual switch instance advertises a single MAC address into the routed Ethernet network so that MAC addresses of the represented dual homed network devices are not required to be advertised into the routed Ethernet network.

9. The method of claim 7, wherein each virtual switch instance represents a set of dual homed network devices with similar failover characteristics.

10. The method of claim 1, wherein each of the dual homed network devices is an Ethernet switch unit.

11. The method of claim 1, wherein control packets received from one of the multiple dual homed network devices will be U-turned to be output toward another of the multiple dual homed network devices so that the control packets follow a logical ring, while data packets from the one of the multiple dual homed network devices will be forwarded directly onto the routed Ethernet network.

12. A data center, comprising:
 a plurality of Ethernet switch units, each of the plurality of Ethernet switch units providing connectivity to a plurality of servers;
 at least two gateways providing connectivity between the Ethernet switch units and a routed Ethernet network, each of the gateways implementing at least one instance of a virtual switch to summarize MAC addresses of represented Ethernet switch units into the routed Ethernet network;
 communication links extending between each of the Ethernet switch units and the at least two gateways to enable each Ethernet switch unit to be dual homed on the at least two gateways so that the Ethernet switch unit is provided with redundant connectivity to the routed Ethernet network; and
 wherein at least one separate Ethernet ring control protocol instance is implemented within the data center for each of the Ethernet switch units to coordinate representation of the Ethernet switch units by the virtual switches into the routed Ethernet network, wherein each virtual switch instance participates in multiple separate Ethernet ring control protocol instances to enable the virtual switch to represent multiple Ethernet switch units into the routed Ethernet network.

13. The data center of claim 12, wherein a separate Ethernet ring control protocol instance is implemented for sets of multiple Ethernet switch units.

14. The data center of claim 13, wherein control packets received from one of the Ethernet switch units will be U-turned to be output toward another Ethernet switch unit so that the control packets follow a logical ring, while data packets from the one of the Ethernet switch units will be forwarded directly onto the routed Ethernet network.

15. A method of implementing control of multiple network devices, the multiple network devices being physically dual homed on a same pair of gateways configured to provide interconnectivity between the multiple network devices and a routed Ethernet network, the method comprising the steps of:
 implementing, by each gateway, at least one virtual switch instance to represent the multiple dual homed network devices into the routed Ethernet network, each virtual switch instance having a corresponding media access control (MAC) address; and
 implementing at least one ring-based control protocol instance between the virtual switch instances and the multiple dual homed network devices to enable the virtual switch instances to coordinate representation of the multiple dual homed network devices into the routed Ethernet network such that each of the multiple dual homed network devices is represented into the routed Ethernet network using one of the corresponding MAC addresses based on control packets distributed in the at least one ring-based control protocol instance.

16. A method of implementing control of multiple network devices, the multiple network devices being physically dual homed on a pair of gateways configured to provide interconnectivity between the multiple network devices and a routed Ethernet network, the method comprising the steps of:
 implementing, by each gateway, at least one virtual switch instance to represent the multiple dual homed network devices into the routed Ethernet network; and
 implementing at least one ring-based control protocol instance between the at least one virtual switch instance of each gateway and the multiple physically dual homed network devices to enable the virtual switches to coordinate representation of the dual homed network devices into the routed Ethernet network, wherein control packets received from one of the multiple dual homed network devices will be U-turned to be output toward another of the multiple dual homed network devices so that the control packets follow a logical ring, while data packets from the one of the multiple dual homed network devices will be forwarded directly onto the routed Ethernet network.

* * * * *